(12) United States Patent
Boddenberg et al.

(10) Patent No.: US 9,873,858 B2
(45) Date of Patent: Jan. 23, 2018

(54) MIXING DEVICE FOR HOMOGENIZATION OF CELL SUSPENSIONS

(71) Applicant: Miltenyi Biotec GmbH, Bergisch Gladbach (DE)

(72) Inventors: Jan Boddenberg, Cologne (DE); Stefan Miltenyi, Bergisch Gladbach (DE); Frederik Fritzsch, Cologne (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 267 days.

(21) Appl. No.: 14/721,468

(22) Filed: May 26, 2015

(65) Prior Publication Data

US 2015/0344832 A1 Dec. 3, 2015

(30) Foreign Application Priority Data

Jun. 2, 2014 (DE) .................. 10 2014 210 340

(51) Int. Cl.
| | | |
|---|---|---|
| *B01F 7/00* | (2006.01) | |
| *B01F 13/00* | (2006.01) | |
| *C12M 1/06* | (2006.01) | |
| *B01F 7/16* | (2006.01) | |
| *B01F 13/08* | (2006.01) | |
| *B01F 7/22* | (2006.01) | |
| *B01F 13/10* | (2006.01) | |

(52) U.S. Cl.
CPC .......... *C12M 27/02* (2013.01); *B01F 7/00183* (2013.01); *B01F 7/00225* (2013.01); *B01F 7/00341* (2013.01); *B01F 7/162* (2013.01); *B01F 7/22* (2013.01); *B01F 13/0827* (2013.01); *B01F 13/0863* (2013.01); *B01F 13/1022* (2013.01); *B01F 2215/0073* (2013.01)

(58) Field of Classification Search
CPC .............. B01F 13/0845; B01F 13/0863; B01F 7/00341; B01F 7/162; B01F 13/0827; C12M 27/02

See application file for complete search history.

(56) References Cited

U.S. PATENT DOCUMENTS

| | | | |
|---|---|---|---|
| 3,168,294 A | | 2/1965 | Hasamura |
| 4,465,377 A | * | 8/1984 | de Bruyne .......... B01F 13/0818 366/273 |
| 6,461,034 B1 | * | 10/2002 | Cleveland ........... B01F 7/00291 366/273 |

(Continued)

FOREIGN PATENT DOCUMENTS

| | | |
|---|---|---|
| DE | 900542.5 | 12/1940 |
| DE | 90 06 542 | 9/1990 |

(Continued)

*Primary Examiner* — Tony G Soohoo
*Assistant Examiner* — Anshu Bhatia
(74) *Attorney, Agent, or Firm* — Jaquelin K. Spong

(57) ABSTRACT

The invention is directed to a homogenization device for cell suspensions, comprising a first rotating magnet; a shaft on which a propeller mixer is attached which rotates around the longitudinal axis of the shaft and is movable in lateral direction of the axis of the shaft; the propeller mixer being provided with at least two propeller blades of which at least one is provided with a second magnet; wherein the propeller mixer is rotated by magnetic interaction of the second magnet with the first rotating magnet.

15 Claims, 4 Drawing Sheets

(56) References Cited

U.S. PATENT DOCUMENTS

| | | | |
|---|---|---|---|
| 2007/0091716 A1* | 4/2007 | Zeikus | B01F 3/04113 366/104 |
| 2008/0131957 A1* | 6/2008 | Ryan | B01F 7/1695 435/289.1 |
| 2014/0034555 A1 | 2/2014 | Foster et al. | |
| 2014/0133265 A1* | 5/2014 | Francis | B01F 13/0863 366/273 |

FOREIGN PATENT DOCUMENTS

| | | |
|---|---|---|
| DE | 44 13 463 A1 | 10/1995 |
| DE | 4413463 | 10/1995 |
| DE | 10 2006 014 471 A1 | 10/2007 |
| DE | 10200601447 | 10/2007 |
| DE | 102006014471 | 10/2007 |
| EP | 0259002 | 3/1988 |
| WO | WO 2015/132317 | 9/2015 |

* cited by examiner

MIXING DEVICE FOR HOMOGENIZATION OF CELL SUSPENSIONS

CROSS REFERENCE TO RELATED APPLICATIONS

This application claims priority to German Application No. DE 102014210340.1, filed Jun. 2, 2014, the content of which is incorporated herein by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention is directed to a mixer for homogenization of cell suspensions.

It is essential for research or diagnosis of living cells to provide the cell in suspension. Otherwise, supply of nutrition or gases may be restricted to diffusion, unwanted cell-cell interaction occurs and/or processing steps like counting or analysis of the cells is hampered.

It is long known to suspend cells by mechanical mixing or stifling. For suspending cells in laboratory scale, it is furthermore known to use magnetic mixing, which are driven by interaction with an external, rotating magnet. Mechanical and magnetic mixing of cells suspensions are for example disclosed in DE4413463, DE900542.5 or DE10200601447.

The downside of the known systems is that the magnetic propellers either are in physical contact with the surface (bottom) of the mixing vessel or are not able to homogenously stir the whole volume of the cell suspension, especially in tube-like mixing vessels or are not appropriate for liquid volumes of less than 50 μl.

SUMMARY

Accordingly it is an object of the invention to provide a means for homogenization of cell suspensions, suitable for small volumes and/or tube-like mixing vessels without the need of complex mechanical impulsion.

Object of the invention is a homogenization device for cell suspensions, comprising a first rotating magnet; a shaft on which a propeller mixer is attached which rotates around the longitudinal axis of the shaft and is movable in lateral direction of the axis of the shaft; the propeller mixer being provided with at least two propeller blades of which at least one is provided with a second magnet; wherein the propeller mixer is rotated by magnetic interaction of the second magnet with the first rotating magnet.

The homogenization device according to the invention is especially useful for suspending biological sample like cells in a aqueous medium or is systems for processing cells, like sorting, detecting or counting cells where the cells need to stay for longer periods of time in a homogenous suspension.

The homogenization device comprises a propeller mixer with a through-hole wide enough to ensure unhindered movement of the propeller mixer on the shaft. The propeller mixer and the shaft have no mechanical connection. However, in order to prevent the propeller mixer from contacting the surface of the mixing vessel and/or leaving the shaft, it is preferred that the shaft is provided with means to stop the lateral movement of the propeller on the ends of the shaft. The shaft is preferably made from a non-flexible, non-bendable material like stainless steel and should have a constant diameter over its entire length. The shaft is not provided with a threat or the like for turning the rotational movement of the propeller into lateral movement on the shaft.

The homogenization device of the invention is able to homogenize rather small volumes of liquid, like about 50 μl, up to larger volumes like 100 ml. Due to the lateral movement of the propeller mixer controlled by the rotational speed of the first magnet, homogenization is achieved over the whole volume of the liquid/sample thus avoiding no-mixing zones.

DETAILED DESCRIPTION

The first, rotating magnet provides a rotating magnetic field which drives the propeller by magnetic interaction with the second magnet(s). It is preferred that the rotational speed of the first, rotating magnet is substantionally the same as the rotational speed of the propeller.

The homogenization device comprises a propeller mixer with preferably 2 or 4 blades, of which at least one is provided with a second magnet. The other blades are either provided with a further second magnet or a counter weight to avoid unbalances. The second magnets or counter weights should have essentially the same weight. Preferably, the homogenization device comprises a propeller mixer with two 2 blades, where each blade is provided with a second magnet.

Figure 1:
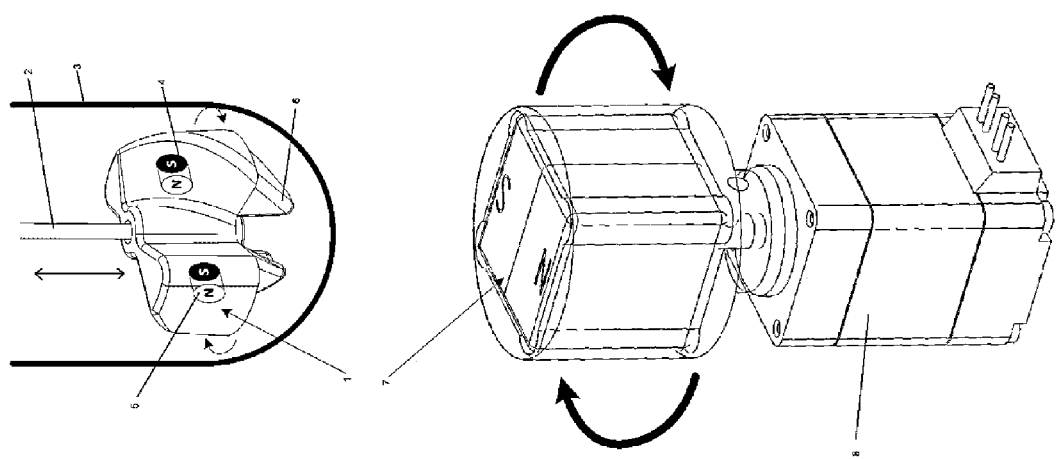
FIG. 1 shows an embodiment of the homogenization device comprising propeller mixer (1), shaft (2), mixing vessel (3), second magnet (4) and (5), conical shaped propeller blade (6), first magnet (7), electric drive (8)

This embodiment (as shown in FIG. 1), the second magnets have preferably an alternating orientation of the respective magnetic poles. i.e. north and south pole are facing each other, providing macroscopically a single magnetic field. In this embodiment it is further preferred that the second magnets are provided at the same lateral position in the propeller blades to ensure an homogenous magnetic field. Furthermore and as shown in FIG. 1, the magnetic poles of the second magnets shall be oriented towards the shaft and not parallel to the axis of rotation.

Preferably, the second magnets and the counterweights are embedded in the propeller blades to ensure that ferromagnetic alloys can be used which provide a large magnetic field but are prone to fast corrosion. Preferably, the second magnets are embedded by 0.2 to 1 mm, more preferably by 0.4 to 0.8 mm of non-magnetizable material.

The propeller consists preferably of non-magnetizable material which prevents magnetically labeled cells from adhering to the propeller. As non-magnetizable material used for manufacturing the propeller mixer, any polymer which is water-insoluble and capable of being injection-molded can be used. Suitable materials are for example poly ethylene, poly propylene, poly styrene, PTFE or the like.

Providing the mixer with magnets integrated or embedded in the propeller blades reduces local magnetic gradients and enhances the magnetic coupling to the first magnet providing the force to rotate and vertical movement of the propeller on the shaft. The variant of the invention comprising two second magnets in a propeller mixer having two blades enables a symmetric design of the propeller with low mass of the magnets.

The shape of the propeller shall ensure homogenous mixing or homogenization of the cell suspension. For this propose, various forms and shapes of the propeller and the blades can be utilized. In the present invention, propeller blades are preferred which are inclined to the axis of rotation thereby enabling the movement of the propeller on the shaft. The propeller mixer moved in lateral direction of the axis of the shaft by adjusting the rotational speed of the rotating, first magnet. The direction and speed of the rotation of the first magnet defines the direction of the movement of the propeller on the shaft and finally the speed of the mixing process.

The shaft and the first magnet can be located in any orientation to each other as long as the rotation of the first magnet is induced by magnetic interaction on the propeller mixer. Accordingly, the first rotation magnet and the shaft may share any angle between 0 and 90°, i.e. the first rotation magnet and the shaft may by aligned coaxial or orthogonal.

In a preferred embodiment of the invention, the propeller and the blades are cone- or peak-shaped perpendicular to the plane of rotation with an angle of 1 to 180°, preferred 45 to 90°, in order to mix small volumes of liquid in vessels having a pointed (like Falcon® tubes) or round bottom as shown in FIG. 1. Furthermore, opposing propeller blades can be tilted against each other in order to enhance lateral movement of the propeller on the shaft.

The propeller of the homogenization device of the invention has preferably a diameter in the plane of rotation of about 2-50 mm. Since the propeller mixer moves along the shaft, even homogenization of suspensions provided in long, tub-like vessels like Falcon® tubes can be be achieved. Depending on the speed of rotation, different volumes of the vessel are mixed. If the speed of rotation is low, the lower parts of the vessel are mixed. By increasing the speed of rotation of the first magnet and by way of magnetic interaction of the propeller mixer, the propeller moves along the shaft to one end of the vessel, for example the upper parts of the vessel. Of course, by decreasing the speed of rotation of the first magnet, the propeller mixer moves along the shaft to the opposite end of the vessel, like the bottom.

The orientation of the first rotating magnet and the propeller mixer in view of the mixing vessel is not of particular importance. In a first variant, at least one mixing vessel having a cover and a bottom is provided and wherein the shaft is attached to the cover of the mixing vessel and the first rotating magnet is located adjacent to the cover of the mixing vessel. In a second variant, at least one mixing vessel having a cover and a bottom is provided and wherein the shaft is attached to the bottom of the mixing vessel and the first rotating magnet is located adjacent to the bottom of the mixing vessel.

Figure 3:
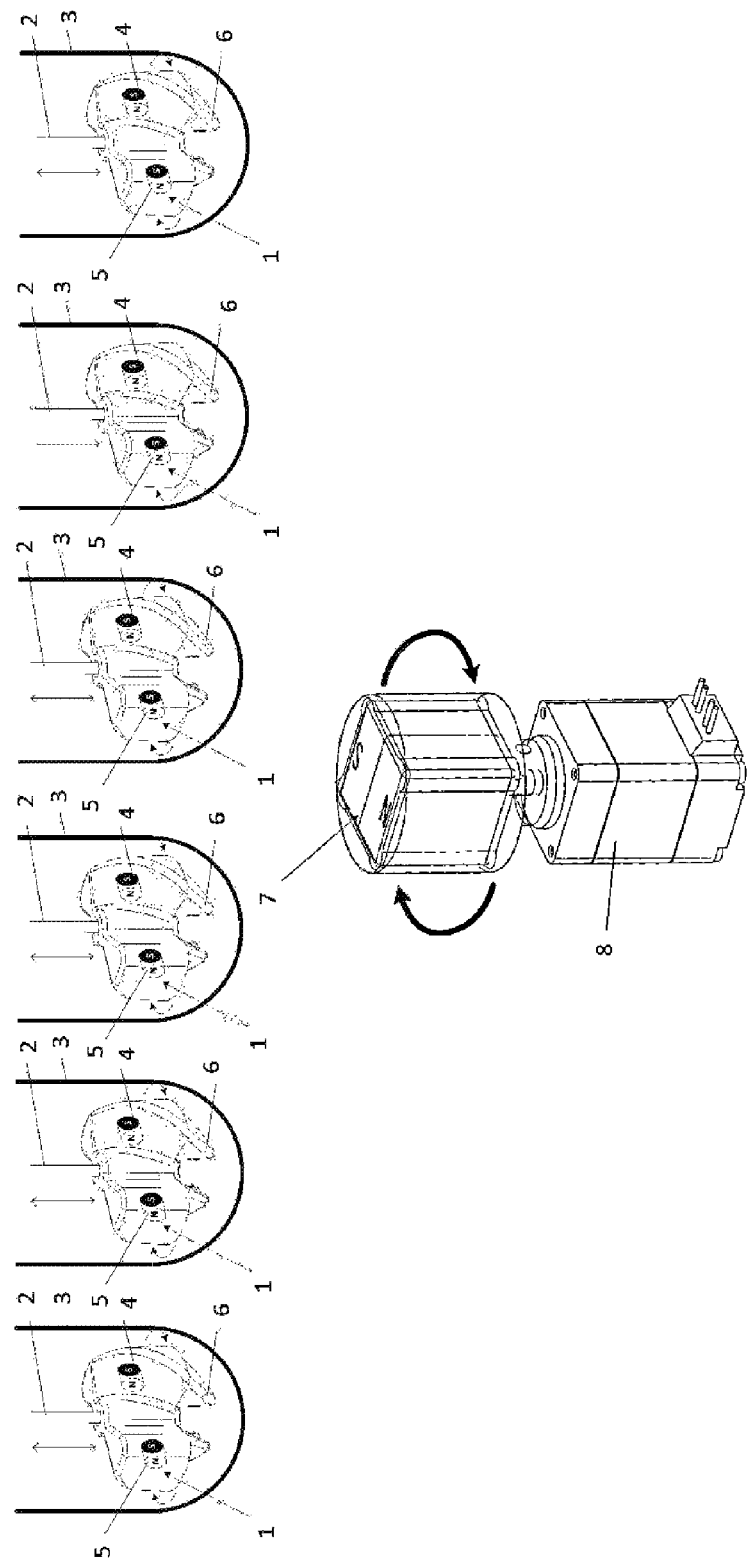
FIG. 3 shows the parallelization of a mixing or homogenization process with several homogenization devices and mixing vessels powered by one first rotating magnet.

It is possible, that a single first magnet drives a plurality (like 5 to 100) of homogenization devices in a parallel fashion as shown in FIG. 3. Accordingly, the homogenization device of the invention may comprise one first rotating magnet and at least two shafts, each provided with a propeller which rotates around the longitudinal axis of the respective shaft, wherein each propeller is movable in lateral direction of the axis of the respective shaft and each propeller is provided with at least two propeller blades of which at least one is provided with a second magnet wherein the propeller is put in rotation by magnetic interaction of the second magnet wherein with the with the first rotating magnet.

Figure 4:
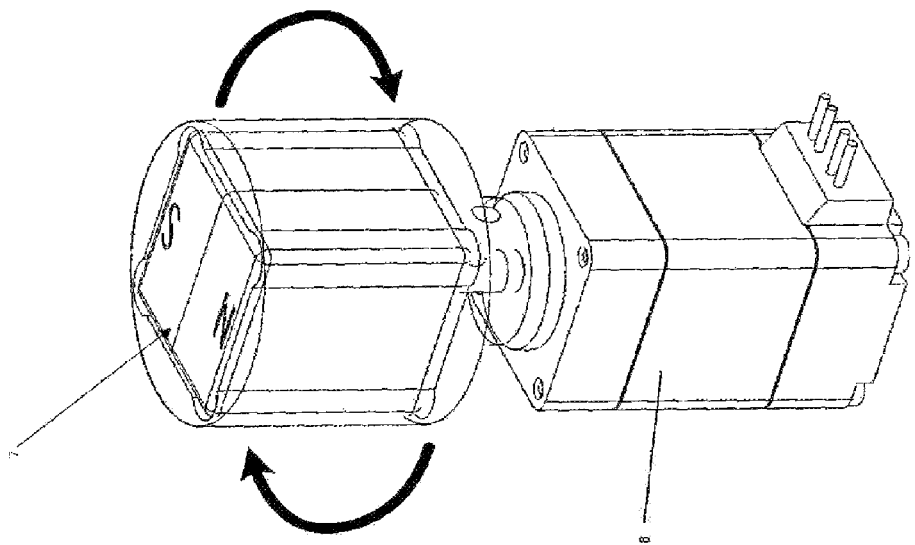
FIG. 4 shows an embodiment of the homogenization device wherein propeller mixer (1) and first magnet (7) are aligned orthogonal to each other.
Figure 4:
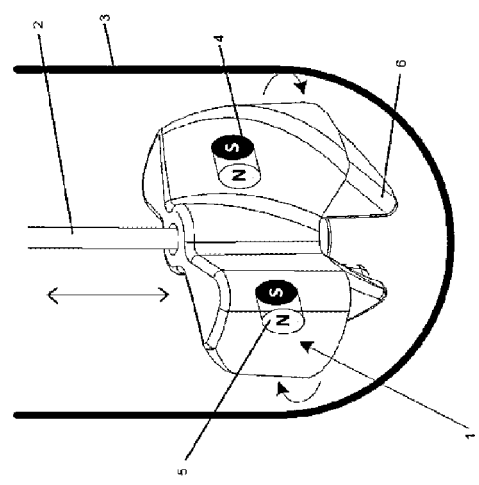

FIG. 4 shows an embodiment of the homogenization device wherein propeller mixer (1) and first magnet (7) are aligned orthogonal to each other.

The distance of the propeller mixer/the second magnet to the first rotation magnet can be as large 1 to 200 mm or 40 mm to 80 mm (FIG. 1 is not to scale) and can be adjusted according to the strength of the magnetic field provided by the first magnet.

The first magnet can be made from the same magnetic material as the second magnet and is rotated by a small electric motor ((8) in FIG. 1). In order to regulate the speed of rotation of the propeller mixer, the speed of the electric motor should be adjustable. In the variant of the invention where one first rotating magnet powers one propeller mixer, both axis of rotation should be aligned.

Figure 2:
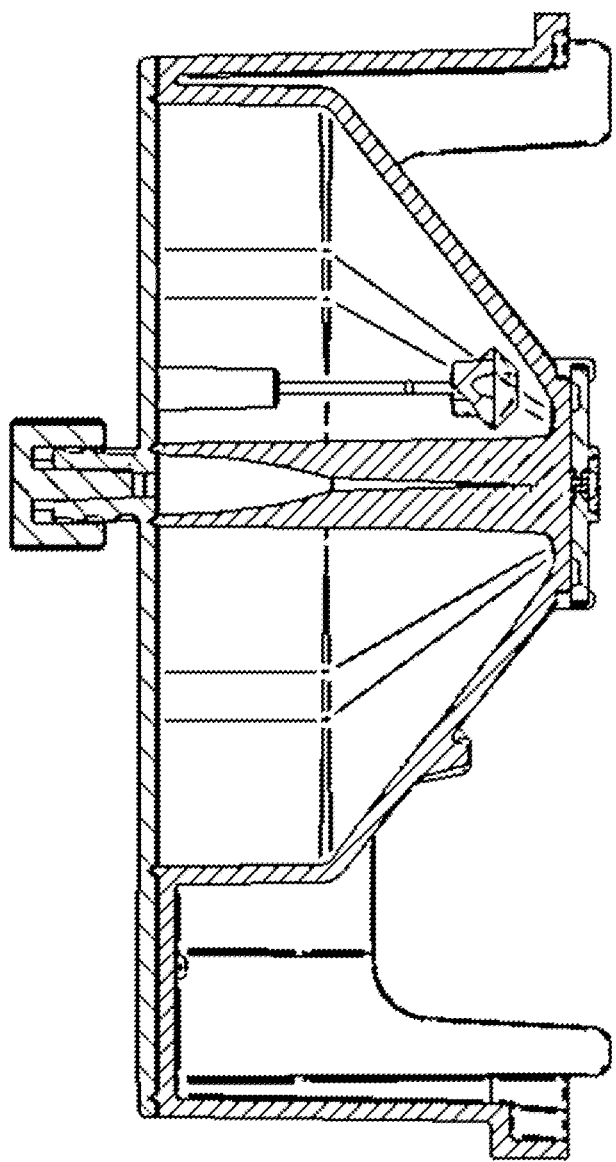
FIG. 2 shows the integration of the homogenization device into a closed mixing vessel.

FIG. 2 shows the use of a mixer according to the invention within a complex shaped mixing vessel. If the bottom of the mixing vessel is flat, the shape of the propeller blades should be rather flat too in order to ensure homogenization at the bottom of the vessel. The first magnet may be located above or below the vessel.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A homogenization device for cell suspensions, comprising:
    a first rotating magnet;
    a shaft on which a propeller mixer is attached, which rotates around the longitudinal axis of the shaft and is movable in a lateral direction of the axis of the shaft;
    wherein the propeller mixer is provided with at least two propeller blades of which at least one is provided with a second magnet; wherein the propeller mixer is rotated by magnetic interaction of the second magnet with the first rotating magnet.

2. The homogenization device according to claim 1, characterized in that the propeller mixer is provided with two propeller blades, each blade having a single magnet.

3. The homogenization device according to claim 2, characterized in that the magnet in each propeller blades is oriented with alternating poles.

4. The homogenization device according to claim 1, characterized in that the propeller mixer is moved in the direction of the axis of the shaft by adjusting a rotational speed of the first rotating magnet.

5. The homogenization device according to claim 1, characterized in that the shaft and the first rotating magnet are aligned coaxial.

6. The homogenization device according to claim 1, characterized in that the propeller mixer has a diameter perpendicular to the longitudinal axis of the shaft of 2-50 mm.

7. The homogenization device according to claim 1, characterized in that at least one mixing vessel having a cover and a bottom is provided and wherein the shaft is attached to the cover of the mixing vessel and the first rotating magnet is located adjacent to the cover of the mixing vessel.

8. The homogenization device according to claim 1, characterized in that at least one mixing vessel having a cover and a bottom is provided and wherein the shaft is attached to the bottom of the mixing vessel and the first rotating magnet is located adjacent to the bottom of the mixing vessel.

9. The homogenization device according to claim 1, characterized in that the second magnet is embedded in the propeller blades.

10. The homogenization device according to claim 1, wherein the propeller blades which are inclined to the axis of rotation, and configured to enable the movement of the propeller on the shaft.

11. The homogenization device according to claim 1, wherein the propeller blades are cone- or peak-shaped perpendicular to the plate of rotation with an angle of 1° to 180°.

12. The homogenization device according to claim 1, wherein the propeller blades are configured to mix small volumes of liquid in vessels having a pointed or round bottom.

13. The homogenization device according to claim 1, wherein opposing propeller blades are tilted against each other, enhancing movement of the propeller on the shaft.

14. The homogenization device according to claim 1, wherein the propeller mixer and the shaft have no mechanical connection.

15. A homogenization device for cell suspensions, comprising:
   a first rotating magnet;
   a shaft on which a propeller is attached, which rotates around the longitudinal axis of the shaft and is movable in a direction of the axis of the shaft;
   wherein the propeller is provided with at least two propeller blades of which at least one is provided with a second magnet; wherein the propeller is rotated by magnetic interaction of the second magnet with the first rotating magnet.

* * * * *